United States Patent [19]
Gillard et al.

[11] Patent Number: 5,182,367
[45] Date of Patent: Jan. 26, 1993

[54] 5-LIPOXYGENASE ACTIVATING PROTEIN

[75] Inventors: John W. Gillard, Baie D'Urfe; Jacques-Yves Gauthier, Laval; Jillian F. Evans, St. Lambert; Rejean Fortin, Montreal Nord; Yvan Guinon, Montreal, all of Canada; Richard A. F. Dixon, Houston, Tex.; Douglas K. Miller, Westfield, N.J.

[73] Assignees: Merck & Co., Inc., Rahway, N.J.; Merck Frosst Canada, Inc., Kirkland, Canada

[21] Appl. No.: 618,449

[22] Filed: Nov. 30, 1990

Related U.S. Application Data

[63] Continuation-in-part of Ser. No. 451,268, Dec. 15, 1989, abandoned.

[51] Int. Cl.⁵ ............................................. C07K 13/00
[52] U.S. Cl. .................................... 530/350; 424/85.8
[58] Field of Search ....................... 530/350; 424/85.8

[56] References Cited

PUBLICATIONS

Dixon et al. *Nature* 343:282-284 (1990).
Miller et al. *Nature* 343:278-281 (1990).

*Primary Examiner*—Garnette D. Draper
*Assistant Examiner*—Shelly J. Guest
*Attorney, Agent, or Firm*—Gabriel Lopez; Joseph F. DiPrima

[57] ABSTRACT

An 18kD protein (FLAP) has been isolated from rat and human cells which is necessary for production of leukotrienes from arachidonic acid in mammalian cells containing 5-lipoxygenase. The gene (cDNA) encoding for FLAP has also been produced.

3 Claims, 1 Drawing Sheet

```
                                            MDQEtVGNVV
HUMAN      GCAGTCCTCTCTGGGGAGCCTGAAGCAAACATGGATCAAGAAACTGTAGGCAATGTTGTC
  -30      ||  ||||   |  |||| |||||||||||||||| ||||  |||||||||||||||
           ACTAGTTGTCTCTGGGGAGCCTGAGCAAGCATGGATCAAGAGGCTGTGGGCAATGTTGTG
RAT                                         M D Q E a V G N V V

HUMAN      L L A I V T L I S V V Q N g F F A H K V
           CTGTTGGCCATCGTCACCCTCATCAGCGTGGTCCAGAATGGATTCTTTGCCCATAAAGTG
  31       || |||||||||||||||||||||||||||||||||| |  |||||| ||||| || |||
           CTCCTGGCCATCGTCACCCTCATCAGCGTGGTCCAGAACGCATTCTTCGCCCACAAGGTG
RAT        L L A I V T L I S V V Q N a F F A H K V

HUMAN      E h E S r t Q n G R S F Q R T G T L A F
           GAGCACGAAAGCAGGACCCAGAATGGGAGGAGCTTCCAGAGGACCGGAACACTTGCCTTT
  91       ||||  |||||  ||| | || |   ||||||||||||||||| ||  ||  ||||||||
           GAGCTTGAAAGCAAGGCGCAAAGCGGGAGAAGCTTCCAGAGGACGGGGACTCTTGCCTTC
RAT        E l E S k a Q s G R S F Q R T G T L A F

HUMAN      E R V Y T A N Q N C V D A Y P T F L a V
           GAGCGGGTCTACACTGCCAACCAGAACTGTGTAGATGCGTACCCCACTTTCCTCGCTGTG
  151      ||||||||||||||||||||||||||| ||||||||||||||||||||||||| |  ||
           GAGCGGGTCTACACTGCCAACCAGAACTGCGTAGATGCGTACCCCACTTTCCTTGTGGTA
RAT        E R V Y T A N Q N C V D A Y P T F L v V

HUMAN      L W s A G L L C S Q V P A A F A G L M Y
           CTCTGGTCTGCGGGGCTACTTTGCAGCCAAGTTCCTGCTGCGTTTGCTGGACTGATGTAC
  211      ||||||  ||||  || |||||||||||||||  || ||  |||  ||||| ||||||||
           CTCTGGACTGCAGGACTACTTTGCAGCCAAGTCCCCGCCGCCTTCGCTGGGCTGATGTAT
RAT        L W t A G L L C S Q V P A A F A G L M Y

HUMAN      L F V R Q K Y F V G Y L G E R T Q S T P
           TTGTTTGTGCGGCAAAAGTACTTTGTCGGTTACCTAGGAGAGAGAACGCAGAGCACCCCT
  271      |||| |||  |||||||||||||||| || || ||||||||||||||||| |||||||||
           CTGTTCGTGAGGCAAAAGTACTTTGTCGGCTATCTGGGAGAGAGAACTCAGAGCACCCCT
RAT        L F V R Q K Y F V G Y L G E R T Q S T P

HUMAN      G Y I F G K R I I L F L F L M S v A G I
           GGCTACATATTTGGGAAACGCATCATACTCTTCCTGTTCCTCATGTCCGTTGCTGGCATA
  331      |||||||||| ||  || || ||||| ||||| |||||||||||| | ||| || ||||
           GGCTACATATTCGGCAAGCGGATCATCCTATTCTTGTTCCTCATGTCCCTTGCCGGCATC
RAT        G Y I F G K R I I L F L F L M S l A G I

HUMAN      f N y Y L I F F F G S D F E N Y I k T I
           TTCAACTATTACCTCATCTTCTTTTTCGGAAGTGACTTTGAAAACTACATAAAGACGATC
  391      ||||| ||||||||||||||| || ||||||| ||||| |||||||||||| |  ||||
           CTCAACCATTACCTCATCTTCTTCTTCGGAAGCGACTTCGAGAACTACATTAGAACTATA
RAT        l N h Y L I F F F G S D F E N Y I r T I

HUMAN      s T T I S P L L L I P *
           TCCACCACCATCTCCCCTCTACTTCTCATTCCCTAACTCTCTGCTGAATATGGGGTTGGT
  451      ||||| || ||||||||| || |||||||||| |||  |   | |  |   ||  |  |
           ACCACGACGATCTCCCCCGCTGCTTCTCATCCCCTGATGGCTGGATACCGGAGTAGGACGA
RAT        t T T I S P L L L I p *
```

FIG. 1

5-LIPOXYGENASE ACTIVATING PROTEIN

CROSS-REFERENCE

This is a continuation-in-part of U.S. Ser. No. 451,268, Dec. 15, 1989, now abandoned.

BACKGROUND OF THE INVENTION

Several inflammatory diseases, including asthma, arthritis and psoriasis are associated with the production of leukotrienes (LT) by neutrophils, mast cells and macrophages. The initial enzymatic step in the formation of leukotrienes is the oxidation of arachidonic acid by 5-lipoxygenase (5-LO) to leukotriene $A_4$. Osteosarcoma cells transfected with 5-LO express active enzyme in broken cell preparations, but no leukotriene metabolites are produced by these cells when stimulated with the calcium ionophore A23187, indicating that an additional component is necessary for cellular 5-LO activity. Indole leukotriene inhibitors have been described (EP 275,667, Gillard et al.) that inhibit the formation of cellular leukotrienes but have no direct inhibitory effect on soluble 5-LO activity. We have now used these potent agents to identify and isolate a novel membrane protein of relative molecular mass 18,000 which is necessary for cellular leukotriene synthesis.

SUMMARY OF THE INVENTION

An 18kD protein (FLAP) has now been isolated from mammalian (rat and human) cells which is necessary for the cellular production of leukotrienes from arachidonic acid.

The rat and human genes (cDNAs) encoding FLAP have now been isolated. The rat gene (cDNA) has been cloned and used to express FLAP in osteosarcoma cell lines.

DETAILED DESCRIPTION OF THE INVENTION

The indole MK-886 is a known leukotriene biosynthesis inhibitor, described in EP 275,667, Gillard et al. The compound is 3-[1-(4-chlorobenzyl)-3-t-butylthio-5-isopropylindol-2-yl]-2,2-dimethylpropanoic acid.

$^{125}$I-L-669,083 is radiolabeled 3-(1-(4-hydroxy-3-iodobenzyl)-3-(4-azidophenylsulfonyl)-5-isopropylindol-2-yl)-2,2-dimethylpropanoic acid.

L-583,916, 2-(1-p-chlorobenzyl-5-methoxy-2-methylindol-3-yl)propionic acid, is known (U.S. Pat. No. 3,161,654).

L-615,919, 4-chloro-3H-phenothiazin-3-one, is described in U.S. Pat. No. 4,677,032 (Lau et al.). It is a direct inhibitor of 5-LO.

FLAP can be used as an antigen to raise antibodies (polyclonal and monoclonal) which would inhibit FLAP-activated production of leukotrienes.

Because of their activity as leukotriene biosynthesis inhibitors, these antibodies are useful as anti-asthmatic, anti-allergic, and anti-inflammatory agents and are useful in treating allergic rhinitis and chronic bronchitis and for amelioration of skin diseases like psoriasis and atopic eczema. The antibodies are also useful to inhibit the pathologic actions of leukotrienes on the cardiovascular and vascular systems for example, actions such as result in angina or endotoxin shock and also in the treatment of inflammatory and allergic diseases of the eye, including allergic conjunctivitis. They could also be used as cytoprotective agents and for the treatment of migraine headache.

The antibodies may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

FLAP promotes the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus, inhibition of the synthesis of such compounds will alleviate these and other leukotriene-related disease states.

Antibodies to FLAP can also be used in in vitro diagnostic assays to determine FLAP levels in biological samples.

The gene (cDNA) encoding for FLAP can be used for large-scale production of FLAP.

The cellular target of MK-886 was identified by its specific labelling with an $I^{125}$ radio-labelled photoaffinity probe ($^{125}$I-L-669,083) and by its retention on agarose gels to which analogues of MK-886 had been bound. Incubation of $^{125}$I-L-669,083 with neutrophil extracts followed by irradiation with ultraviolet light resulted in the labelling of several proteins; but labelling was only specifically inhibited by MK-886 in the case of a membrane protein of relative molecular mass ($M_r$) 18,000 (18kD). When solubilized extracts of neutrophil membranes (100,000 g-centrifugation pellets) were chromatographed over affinity columns prepared from analogues of MK-886, an 18kD protein found in both rat and human neutrophils was bound and was subsequently eluted by MK-886. This protein co-migrated on SDS-polyacrylamide gels with the photoaffinity-labelled protein. The 18kD protein comprised a minor portion of the 10,000 g-centrifugation pellet protein and was essentially absent from other cellular fractions. The photoaffinity labelling of the 18kD protein was inhibited by MK-886 in a concentration-dependent manner comparable to the inhibition of leukotriene synthesis by this compound; the 50% inhibitory concentration ($IC_{50}$) for photoaffinity labelling by MK-886 is 80 nM, whereas it is 100 nM for inhibition of leukotriene synthesis in human leukocytes at similar protein concentrations. Indole analogues that do not inhibit leukotriene biosynthesis, such as L-583,916, did not inhibit photoaffinity labelling of the 18kD protein, nor did they elute this protein from affinity columns. Several other compounds that have inhibitory effects on leukotriene production (such as nordihydroguairaretic acid, eicosatetraynoic acid, methylisobutylxanthine, and calmodulin antagonists (WF, trifluoroperazine, and calmidazolium)), including direct inhibitors of 5-LO (such as L-651,392, described in Guindon, Y. et al., Adv. in Prostaglandin Thromboxane and Leukotriene Res. 554–557 (Raven, N.Y., 1987)), neither eluted the 18kD protein from the affinity gels nor inhibited photoaffinity labelling of the 18kD protein.

To purify the 18kD protein, the fraction released from the affinity column by MK-886 was chromatographed on a Superose-12 column followed by a subsequent separation on two TSK-3000 columns linked in tandem. After reduction and alkylation, the sample was repurified a second time over the TSK columns, resulting in a single protein peak as shown by silver staining after SDS-PAGE. The total amount of protein isolated from rat peritoneal neutrophils was N1.5 μg/$10^{10}$ cells. N-terminal sequence analysis of the purified rat 18kD protein revealed the single hydrophobic sequence MDQEAVGNVVLLAIVTLISVVQNAFFAXK-VELESKAQSG (single-letter amino-acid code). Cyanogen bromide cleavage of the purified 18kD protein followed by fractionation over a $C_4$ microbore column identified two additional sequences: SLAGILN-HYLIFFFGSDFENY and XLFVXQKYFVGYL-GEXTQ, where X represents an unidentified amino acid. Tryptic cleavage of the 18kD protein blotted onto nitrocellulose followed by separation on a $C_8$ microbore column revealed one unique sequence, XQSTPGYIFGKXIILF. With over half of the predicted number of residues of the 18kD protein contained within the four essentially nonoverlapping peptides described above, there is little sequence homology of this protein to other known proteins.

In the sequences herein, the capital letters have their conventional meaning and represent the following amino acids:

| A | Ala | Alanine |
|---|---|---|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

A polyclonal rabbit antibody was prepared to the N-terminal 39 amino acids of the 18kD protein. The peptide immunogen was prepared by fusion of the DNA sequence coding for the peptide to the N-terminus of Che Y protein, and its expression in and purification from *E. coli* (Gan, Z. R., Gene 79, 159–166 (1989)). Immunoblots with this antibody on rat or human neutrophil 100,000 g-centrifugation pellets or supernatants detected comparable amounts of a single 18kD protein in the membrane fractions. Immunoblots also demonstrated the presence of this protein in membranes of a variety of leukocyte cell lines which make leukotrienes, whereas it was present in only trace or undetectable amounts in other cell lines which lack the ability to synthesize leukotrienes. When human leukocyte membranes labelled with the $^{125}$I-L-669,083 photoaffinity probe were immunoprecipitated with the antipeptide antibody, a single labelled protein of $M_r$ 18,000 was observed which was absent in membranes labelled in the presence of competing MK-886. These results confirm that the protein identified by the photoaffinity probe is identical to that isolated by the affinity columns, and that the N-terminal sequence is derived from that protein.

Based on the amino acid sequence of purified rat FLAP, cDNA clones approximately 1 kb in length were isolated from rat RBL-1 and human HL60 cell cDNA libraries (FIG. 1). Both the rat and human cDNA clones encode 161 amino acid proteins which are 92% identical and contain all of the peptide sequences derived from purified rat FLAP. Hybridization analysis of RNA from HL60 cells with the cDNA identified a single 1 kb species suggesting that the isolated clones are near full length. Hydropathicity analysis (using the methods of Hopp, T. P. et al., *Proc. Natn. Acad. Sci. U.S.A.* 78, 3824–3828 (1981) and Kyte, J. et al., *J. Molec. Biol.* 157, 105–132 (1982)) of the predicted rat or human FLAP amino acid sequences demonstrated that the proteins are very hydrophobic, consistent with their membrane localization. Of particular interest were three hydrophobic regions of 20–30 residues in length (FIG. 1) which are predicted by hydrophobic moment analysis (Eisenberg, D. et al., *J. Molec. Biol*, 179, 125–142 (1982)) to form membrane spanning alpha helices. Based on these data, a model for the topology of the protein can be proposed in which the 3 transmembrane domains are connected by 2 hydrophilic loops, with the N-terminus and C-terminus of the protein located on opposite sides of the membrane. Comparison of the sequence of FLAP with sequences of other proteins revealed that while FLAP is not identical to any other known protein, a general similarity with several integral membrane proteins was observed. This similarity appears to result from the hydrophobic residues contained within the putative transmembrane regions, however, rather than from any significant primary sequence identity. No concensus sequences for glycosylation, myristyolation, or phosphorylation were identified in the FLAP sequence.

To determine whether FLAP is required for 5-LO function in cells, human osteosarcoma 143 cell lines transfected with the DNA for either FLAP, 5-LO, or FLAP and 5-LO (5-LO/FLAP) were prepared. The expression of the relevant proteins was determined by immunoblots of these cell lines with antisera directed toward FLAP or 5-LO. Parental osteosarcoma 143 cells did not contain detectable levels of either 5-LO protein or FLAP, while the rat neutrophils contained both proteins. The level of 5-LO protein expressed in the transfected 5-LO or 5-LO/FLAP cells was comparable to or slightly higher than that observed in neutrophils. However, the amount of FLAP expressed in the transfected FLAP or 5-LO/FLAP cells was only 20% of the level detected in neutrophils.

When the parental osteosarcoma 143 cells or the cells expressing 5-LO or FLAP alone were treated with the $Ca^{2+}$ ionophore A23187, no arachidonic acid metabolites were detected. In contrast, A23187 treatment of the cell line expressing both 5-LO and FLAP resulted in significant production of 5-LO products, including $LTB_4$ and the $LTA_4$ hydrolysis products 6-trans $LTB_4$ and 6-trans-12-epi $LTB_4$. A23187-treated rat neutrophils produced these products, as well as 5-HETE and the $LTB_4$ metabolites 20-hydroxy $LTB_4$ and 20-carboxy $LTB_4$. The 5-LO/FLAP cell line produced only 14% of the neutrophil level of $LTB_4$ (0.15 nmol/mg protein versus 1.1 nmol/mg protein), while it produced 41% as much of the LTA₄ hydrolysis products (0.064 nmol 6-trans LTB₄ and 0.059 nmol 6-trans-12-epi LTB₄/mg protein versus 0.18 nmol 6-trans LTB₄ and 0.12 nmol 6-trans-12-epi LTB₄/mg protein). These data are consistent with the observation (Evans, J. A. et al., *Biochem. Biophys. Acta* 840, 43–50 (1985)) that the osteosarcoma cells contain only a fraction of the amount of LTA₄ hydrolase that is present in the rat neutrophils. MK-886 and L-615,919 blocked LT synthesis both in the 5-LO/FLAP cell line and in neutrophils.

These experiments clearly demonstrate that the expression of FLAP, together with 5-LO, is essential for cellular LT synthesis and that the activity of the expressed protein is inhibited by MK-886. Although the mechanism by which FLAP causes the activation of 5-LO is not fully understood, FLAP may serve as a membrane anchor for activated 5-LO. According to this model, a stable complex would be required to form at the membrane between activated 5-LO, FLAP, and possibly other components of the LT synthetic pathway, such as phospholipase A₂ or LTA₄ hydrolase. The formation of this complex could regulate the interaction of 5-LO with its substrate, arachidonic acid. However, the invention is not intended to be limited by this theory of mechanism.

The invention is further defined by reference to the following examples, which are intended to be illustrative and not limiting.

EXAMPLE 1

18kD Protein Purification

A. Affinity Column Purification

Rat peritoneal neutrophils (Ham, E. A. et al. *Proc. Natn. Acad. Sci. USA* 80, 4349–4353 (1983)) and human peripheral neutrophils (Boyum, A. *Scand. J. Clin. Lab. Invest.* (suppl. 97) 21, 77–89 (1968)) at $10^8$ cells/ml were sonicated in 50 mM Tris-HCl buffer, pH 7.4, 140 mM NaCl, 2 mM EDTA, 1 mM DTT (dithiotreitol), 10% glycerol (homogenization buffer), together with the protease inhibitors 1 mM phenylmethylsulphonyl fluoride, 2 mg/ml pepstatin, 2 mg/ml leupeptin, and 10 mM furyl saccharine. After removal of 1000 g and 10,000 g-centrifugation pellets, the 100,000 g pellet was resuspended (3 mg/ml) in the homogenization buffer.

To purify FLAP, the microsome suspension was solubilized on ice for 30 minutes in 50 mM Tris-HCl buffer, pH 7.4, with 140 mM NaCl, 0.5 mM DTT, 5% glycerol and 1% CHAPS detergent (3-[(3-cholamidopropyl)-dimethylammonio]-1-propanesulfonate). After centrifugation for 10 minutes at 30,000 g, the supernatant was applied to 3 ml columns ($6 \times 10^9$ cell equivalents per column) containing the affinity gel which was prepared by coupling MK-886 in THF (tetrahydrofuran) to pre-activated Affi-Gel 10, capping with ethanolamine, and washing with isopropanol. The columns were washed with N150 ml solubilization buffer for 16 hours at 5° C. and eluted for 1 hour with four column volumes of buffer containing 100 μM MK-886. To remove detergent and MK-886, samples were vacuum dialysed overnight at 5° C. with a 10 mM Tris-HCl, pH 7.4, 0.25 mM DTT buffer followed by SDS-PAGE (10–20% gradient gels) and visualization by silver staining to show the presence of FLAP.

B. Further Purification

Eluent from Step A was dried by speed-vac (combined centrifugation and lyophilization under vacuum), dissolved in 0.05% SDS-0.1M NH₄HCO₃, and separated on a Superose-12 column eluted with the same buffer at 0.25 ml/min. The fractions containing FLAP were pooled and dried by speed-vac and then dissolved in 0.05% SDS-0.1M NH₄HCO₃. The pool was fractionated over two TSK-3000 columns, linked in tandem and eluted with 0.05% SDS-0.1M NH₄HCO₃ at 0.25 ml/min. The pooled fractions were concentrated and dried by speed-vac. For reduction and alkylation, the sample was suspended in 150 μl of a solution containing 3 μmol DTT in 67 mM Tris-HCl, pH 8.3, incubated for 6 hours at 50° C., and alkylated for 1 hour at 37° C., with 19 μmol iodoacetic acid brought to pH 8.3 with 1M Tris base. DTT was then added to a final concentration of 1M, and the sample incubated overnight at 37° C., dried, and rechromatographed on the TSK-3000 columns to yield pure FLAP as evidenced by a single band on a silver-stained SDS gel and a single sequence on a protein sequenator.

EXAMPLE 2

Flap Sequencing

All cells were grown in Dulbecco's modified minimal essential medium (GIBCO) containing 10% fetal bovine serum. HL60 cells were differentiated by the addition of 1% dimethylsulfoxide and 10 μM dexamethasone and incubation at 37° for 5 days according to the method of Dixon, R. A. F. et al., *Proc. Natn. Acad. Sci. U.S.A.* 85, 416–420 (1988). Poly(A)+ RNA was isolated from RBL-1 cells and differentiated HL60 cells by the guanidinium isothiocyanate-CsCl method (Chargwin, J. M. et al. *Biochemistry* 18, 5294–5299 (1979)) followed by oligo(dT) cellulose chromatography (Aviv, H. et al., *Proc. Natn. Acad. Sci. U.S.A.* 69, 1408–1412 (1972)). Double stranded cDNA was prepared from the poly(A)+ RNA and ligated to lambda ZAP arms (Stratagene) as described in Dixon et al. (1988, supra) and Dixon, R. A. F. et al., *Nature* 321, 75–79 (1986). The DNA was packaged using Gigapack gold (Stratagene) and the resulting phage screened unamplified on *E. coli* strain LE392 as described in Dixon et al. (1988, supra) and Mamiatis, T. et al., Molecular Cloning, A Laboratory Manual, Cold Spring Harbor Laboratories, New York (1982). Pairs of complementary oligonucleotides with 5' extensions (oligonucleotides 5'-ATG GAC CAG GAG GCT GTG GGC AAT GTG GTG CTG CTG GCC ATT GTG ACC CTG ATC TCT GTG GTG CAG and 5'-GCC AGA CTG GGC CTT GGA CTC CAG GGC CAC CTT GTA GGC AAA GAA GGC ATT CTG CAC CAC AGA GAT) corresponding to a sequence capable of encoding each of the rat FLAP derived peptide sequences (N-terminus=M-DQEAVGNVVLLAIVTLISVVQNAFFAXK-VELESKAQSG; CNBr peptide fragments=YLFVX-QKYFVGYLGEXTQS and SLAGILN-HYLIFFFGSDFENY; tryptic peptide fragment=XQSTPPGYIFGKXIILF) were synthesized using an Applied Biosystems 380A DNA synthesizer, annealed, radio-labeled using Klenow DNA polymearse and all four [³²P]dNTPs, and used to screen the RBL-1 cell cDNA library as described in Dixon et al. (1988) and Maniatis et al., both supra. Phage which hybridized to probes corresponding to all of the peptide sequences were purified and the inserts rescued per the manufacturer's (Stratagene) instructions. The cDNA inserts were sequenced completely on both strands as described in Dixon et al. (1988, supra) and Hattori, M. et al., *Anal. Biochem.* 152, 232–238 (1983). Nucleotide sequence analysis of several of the clones revealed a 161 amino acid open reading frame following the first ATG in the sequence. All of the peptide sequences derived from purified rat FLAP were present in the predicted protein sequence. The open reading frame was followed by 408 bp of untranslated sequence ending in a poly(A) tail. The human FLAP cDNA was isolated by using the rat cDNA to probe the dimethylsulfoxide-differentiated HL60 cell cDNA library. Several clones with inserts of approximately 1 kb in length were isolated which contained an open reading frame similar to the one found in rat FLAP cDNA. Similarity searches were performed on the GenBank and EMBL databases and no sequence of primary structure homology was found.

EXAMPLE 3

Expression of 5-LO and Flap in Transfected Cell Lines

Normal rat peritoneal neutrophils were prepared as described by Ham, E. A. et al. (1983, supra). Osteosarcoma 143 cell lines expressing 5-LO were isolated by the method of Rouzer, C. A. et al., *J. Biol. Chem.* 263, 10135–10140 (1988). The expression vector used contains the CMV immediate early promoter which drives the expression of the 5-LO gene, a hygromycin resistance gene as a selectable marker, and the EBV origin of replication (Rouzer et al., supra). An EcoRI fragment derived from the RBL-1 cDNA clone containing the cDNA insert for rat FLAP was cloned into the EcoRI site of the vector pSVLneo (Dixon, R. A. F. et al., *Nature* 326, 73–79 (1987)). This vector contains an SV40 origin of replication and utilizes the SV40 early promoter for expression of the FLAP gene. The vector also contains a neomycin resistance gene as a selectable marker. The FLAP vector was transfected into osteosarcoma 143 cells which were previously transfected with the human 5-LO vector and colonies resistant to both hygromycin and neomycin were isolated according to the methods of Rouzer and Dixon et al. (1987), both supra. The various cell lines were screened for expression of 5-LO and FLAP by immunoblotting with antibodies directed against each protein (Gan and Rouzer, both supra). Because the 5-LO vector is episomal in this cell line and had previously been found to be unstable, (Rouzer, supra), the cell line expressing both 5-LO and FLAP was grown only in the presence of neomycin to allow for loss of the 5-LO gene. Upon passage, a revertant cell line was isolated which retained expression of FLAP, but failed to express 5-LO.

EXAMPLE 4

LT Synthesis by Cells Expressing 5-LO and Flap

Confluent monolayers of osteosarcoma cells ($1 \times 10^7$ cells) or a suspension of rat peritoneal neutrophils ($1 \times 10^8$) were incubated with 4 ml of Hanks phosphate buffered saline containing 15 mM HEPES buffer and 5 μg/ml A23187 ($Ca^{2+}$ ionophore) for 10 min at 37° C. The extracellular fluids were removed, prostaglandin $PGB_2$ was added as an internal standard, and the fluids were acidified with 150 μl of 1N acetic acid. The samples were loaded on to a Step-Pak $C_{18}$ column, washed with 15% methanol and with water, eluted with methanol and dried. The samples were dissolved in 65% methanol/35% $H_2O$/0.05% acetic acid/0.5 mM oxalic acid, pH 5.7, and isocratically separated by chromatography on a Bondpak $C_{18}$ column. The identity of each of the major ultraviolet absorbing species, which included $LTB_4$, was confirmed by coelution with known standards and by spectral analysis. The identity of $LTB_4$ was also confirmed by radioimmune assay.

EXAMPLE 5

Synthesis of $^{125}I$-L-669,083

The methodology herein is similar to that in EP 275,667.

N-Trifluoroacetamido-4-aminothiophenol (I) is reacted with 2,2-dimethyl-4-oxo-5-bromopentanoic acid methyl ester (II) in solvents such as THF with a base such as diisopropylcyclohexylamine to provide 2,2-dimethyl-4-oxo-5-(4-N-trifluoroacetamidophenolthio)-pentanoic acid methyl ester (III). Parahydroxybenzaldehyde (IV) is reacted with pivaloyl chloride and the aldeyde is reduced with sodium borohydride to provide the corresponding 4-pivaloyloxybenzyl alcohol (V) which is converted to the benzyl chloride (VI) with triphenylphosphine and carbon tetrachloride. Reaction of this benzyl chloride with 4-isopropylphenylhydrazine hydrochloride salt in toluene and triethylamine provides the N-benzylated hydrazine (VII). This hydrazine (VII) is condensed with the previously prepared ketone (III) in acetic acid/toluene under reflux to provide the indole (VIII). The trifluoroacetamide group is hydrolyzed with methanol and potassium carbonate to provide the aminophenol (IX) which is then converted to the azide (X) by the action of hydrochloric acid and sodium nitrite followed by the addition of sodium azide. Iodination of this resulting phenolic indole (X) with sodium iodide and chloramine T in dimethylformamide provides the corresponding iodo compound (XI). Oxidation, and hydrolysis of the ester with sodium hydroxide and THF/methanol/water, gives the free acid compound, 3-(1-((4-Hydroxy-3-iodophenyl)methyl)-3-(4-azidophenyl-sulfonyl)-5-isopropylindol-2-yl)-2,2-dimethylpropionic acid, L-669,083 (XII).

The radiolabeled analog is prepared by replacing $Na^{125}I$ for NaI.

An alternative partial synthesis is shown in Method B, where treatment of indole VIII with 2.5 equivalents of m-chloroperbenzoic acid (mCPBA) in $CH_2Cl_2$ at room temperature for 10 hours oxidizes the sulfide to the sulfone (IXa), which is then treated similarly to method A.

METHOD A

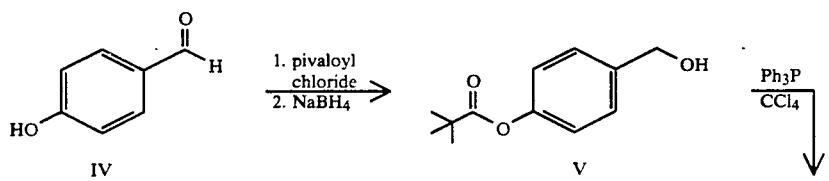

METHOD A
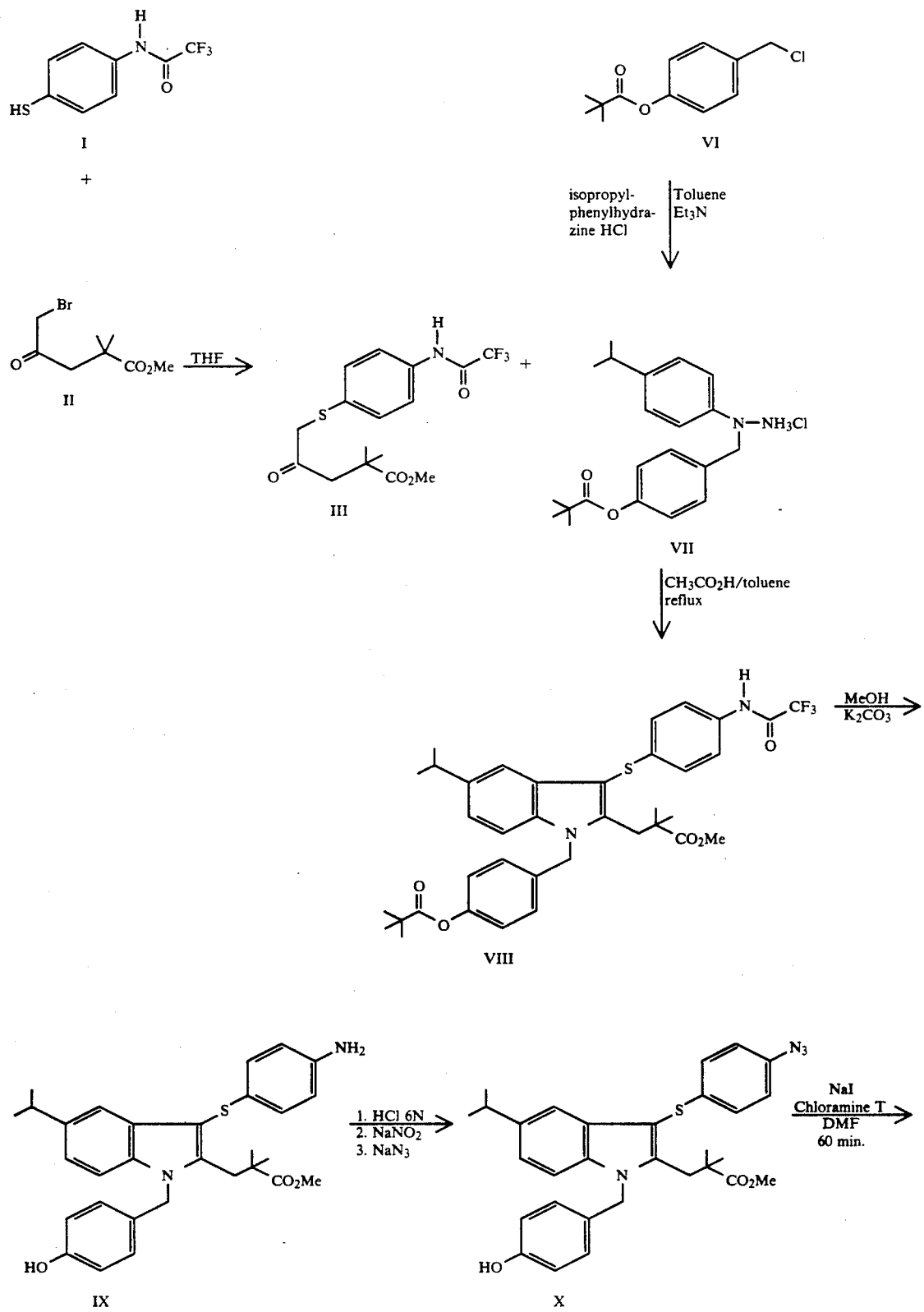

-continued
METHOD A

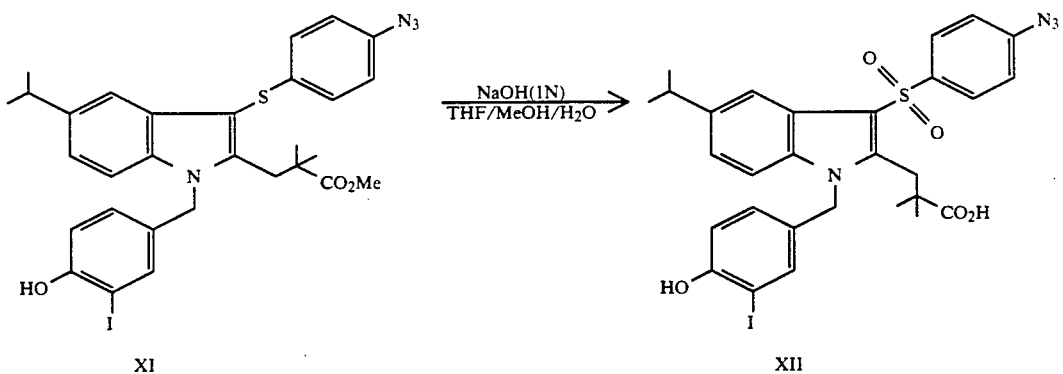

METHOD B

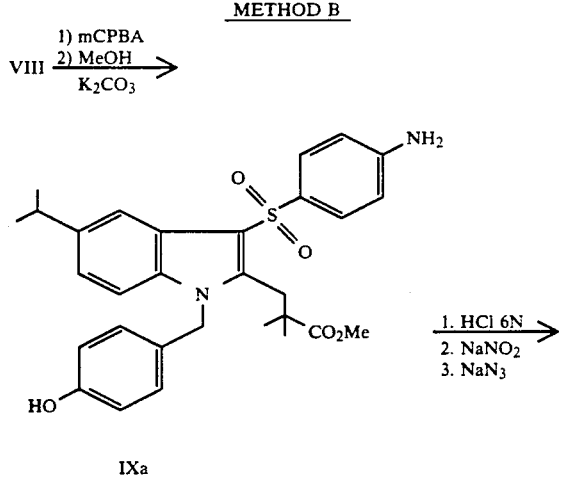

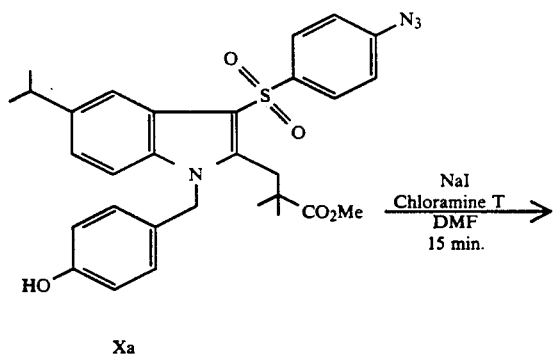

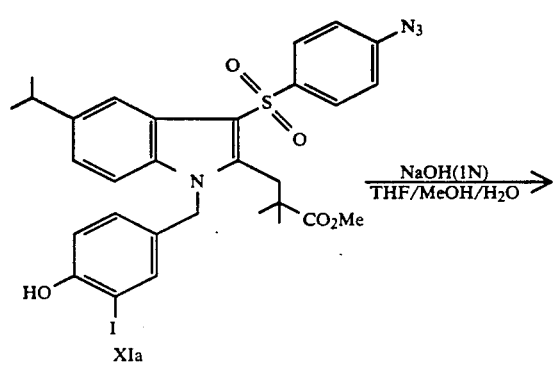

-continued
METHOD B

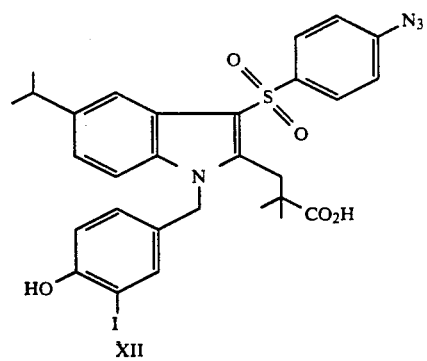

FIGURE 1

The sequences of rat and human FLAP are shown with a comparison of the nucleotide and predicted protein sequences of the rat and human FLAP open reading frames. Numbering begins with the first case of the initiation codon. The termination codon is represented by an asterisk. Nucleotide identity is indicated with the vertical lines. Amino acid identity is indicated with capital letters for identical residues. The hydrophobic regions of the FLAP amino acid sequence which are predicted to be membrane spanning domains are indicated by ~~~~~~~~~~.

What is claimed is:

1. The essentially pure 5-lipoxygenase activating protein (FLAP), characterized in that it has a molecular weight of 18 kD as determined by SDS-PAGE under reducing conditions.

2. A human protein of claim 1, which has the amino acid sequence:

| M | D | Q | E | T | V | G | N | V | V |
|---|---|---|---|---|---|---|---|---|---|
| L | L | A | I | V | T | L | I | S | V |
| V | Q | N | G | F | F | A | H | K | V |
| E | H | E | S | R | T | Q | N | G | R |
| S | F | Q | R | T | G | T | L | A | F |
| E | R | V | Y | T | A | N | Q | N | C |
| V | D | A | Y | P | T | F | L | A | V |
| L | W | S | A | G | L | C | S | Q |
| V | P | A | A | F | A | G | L | M | Y |
| L | F | V | R | Q | K | Y | F | V | G |
| Y | L | G | E | R | T | Q | S | T | P |
| G | Y | I | F | G | K | R | I | I | L |
| F | L | F | L | M | S | V | A | G | I |
| F | N | Y | Y | L | I | F | F | F | G |

-continued

| S | D | F | E | N | Y | I | K | T | I |
|---|---|---|---|---|---|---|---|---|---|
| S | T | T | I | S | P | L | L | L | I |
| P. | | | | | | | | | |

3. A rat protein of claim 1, which has the amino acid sequence:

| M | D | Q | E | A | V | G | N | V | V |
|---|---|---|---|---|---|---|---|---|---|
| L | L | A | I | V | T | L | I | S | V |
| V | Q | N | A | F | F | A | H | K | V |
| E | L | E | S | K | A | Q | S | G | R |

-continued

| S | F | Q | R | T | G | T | L | A | F |
|---|---|---|---|---|---|---|---|---|---|
| E | R | V | Y | T | A | T | N | Q | N | C |
| V | D | A | Y | P | T | F | L | V | V |
| L | W | T | A | G | L | L | C | S | M | Q |
| V | P | A | A | F | A | G | L | M | Y |
| L | F | V | R | Q | K | Y | F | V | G |
| Y | L | G | E | R | T | Q | S | T | P |
| G | Y | I | F | G | K | R | I | I | L |
| F | L | F | L | M | S | L | A | G | I |
| L | N | H | Y | L | I | F | F | T | G |
| S | D | F | E | N | Y | I | R | T | I |
| T | T | T | I | S | P | L | L | L | I |
| P. | | | | | | | | | |

\* \* \* \* \*